(12) United States Patent
Bagherzadeh et al.

(10) Patent No.: US 7,250,543 B2
(45) Date of Patent: Jul. 31, 2007

(54) PREPARATION OF CATALYST AND USE FOR HIGH YIELD CONVERSION OF METHANE TO ETHYLENE

(75) Inventors: Ebrahim Bagherzadeh, Tehran (IR); Abbas Hassan, Sugarland, TX (US); Aziz Hassan, Sugarland, TX (US)

(73) Assignee: HRD Corp., Houston, TX (US)

( * ) Notice: Subject to any disclaimer, the term of this patent is extended or adjusted under 35 U.S.C. 154(b) by 0 days.

(21) Appl. No.: 11/594,678

(22) Filed: Nov. 9, 2006

(65) Prior Publication Data

US 2007/0055083 A1 Mar. 8, 2007

Related U.S. Application Data

(62) Division of application No. 10/833,735, filed on Apr. 28, 2004.

(30) Foreign Application Priority Data

Apr. 29, 2003 (CA) .................................. 2427722

(51) Int. Cl.
*C07C 2/00* (2006.01)
*C07C 2/02* (2006.01)
(52) U.S. Cl. ...................... 585/500; 585/530; 585/700
(58) Field of Classification Search ................. 585/500, 585/530, 700
See application file for complete search history.

(56) References Cited

U.S. PATENT DOCUMENTS

| | | | |
|---|---|---|---|
| 4,200,554 A | 4/1980 | Lauder |
| 4,443,649 A | 4/1984 | Jones et al. |
| 4,523,049 A | 6/1985 | Jones et al. |
| 4,523,050 A | 6/1985 | Jones et al. |
| 4,544,784 A | 10/1985 | Sofranko et al. |
| 4,544,787 A | 10/1985 | Breder, Jr. |
| 4,780,449 A | 10/1988 | Hicks |
| 4,863,971 A | 9/1989 | Broussard et al. |
| 4,939,310 A | 7/1990 | Wade |
| 4,971,940 A | 11/1990 | Kaminsky et al. |
| 5,051,390 A | 9/1991 | Diddams et al. |
| 5,059,740 A | 10/1991 | Kaminsky et al. |
| 5,087,787 A | 2/1992 | Kimble et al. |
| 5,097,086 A | 3/1992 | Lee et al. |
| 5,105,045 A | 4/1992 | Kimble et al. |
| 5,118,654 A | 6/1992 | Choudhary et al. |
| 5,132,481 A | 7/1992 | Do et al. |
| 5,132,482 A | 7/1992 | Smith et al. |
| 5,157,188 A | 10/1992 | Kolts et al. |
| 5,177,294 A | 1/1993 | Siriwardane |
| 5,245,124 A | 9/1993 | Miremadi et al. |
| 5,262,551 A | 11/1993 | Horrell, Jr. et al. |
| 5,321,185 A | 6/1994 | Van der Vaart |
| 5,321,188 A | 6/1994 | Fornasari et al. |
| 5,354,936 A | 10/1994 | Yamamura et al. |
| 5,386,074 A | 1/1995 | Durante et al. |
| 5,430,209 A | 7/1995 | Agaskar et al. |
| 5,430,219 A | 7/1995 | Sanfilippo et al. |
| 5,625,107 A | 4/1997 | Park et al. |
| 5,695,618 A | 12/1997 | O'Young et al. |
| 5,763,722 A | 6/1998 | Vic et al. |
| 5,849,973 A | 12/1998 | Van Der Vaart |
| 5,877,387 A | 3/1999 | Park et al. |
| 5,880,320 A | 3/1999 | Netzer |
| 5,883,038 A | 3/1999 | Park et al. |
| 5,900,521 A | 5/1999 | Park et al. |
| 6,096,934 A | 8/2000 | Rekoske |
| 6,130,260 A | 10/2000 | Hall et al. |
| 6,166,283 A | 12/2000 | Bharadwaj et al. |
| 6,323,247 B1 | 11/2001 | Hall et al. |
| 6,596,912 B1 | 7/2003 | Lunsford et al. |
| 6,602,920 B2 | 8/2003 | Hall et al. |
| 2001/0004533 A1 | 6/2001 | Yamamoto et al. |
| 2001/0026865 A1 | 10/2001 | Miyoshi et al. |
| 2002/0000085 A1 | 1/2002 | Hall et al. |
| 2002/0007101 A1 | 1/2002 | Senetar et al. |
| 2002/0035305 A1 | 3/2002 | Ichikawa et al. |
| 2002/0150531 A1 | 10/2002 | Ohmori et al. |

*Primary Examiner*—J. Parsa
(74) *Attorney, Agent, or Firm*—Thomas L. Adams; Benjamin Appelbaum

(57) ABSTRACT

A perovskite catalyst is prepared using a ceramic sol-sol methodology comprising preparing slurry in water of an alkaline earth metal salt, a powdered metal salt and a powdered transition metal oxide, adding a polymeric binder to form a paste, drying and comminuting the paste into a powder and heating the powder with a temperature profile to calcination temperatures. In one embodiment the slurry is formed of titanium oxide with barium carbonate and tin chloride in deionized water, and more specifically by a mixture according to Ba (1-0.05x)+TiO2+SnCl2(0.05x) where x is in moles. The perovskite catalyst is preferably used in a process for oxidative coupling of methane. Catalyst performance is enhanced through the addition of halides to the feed gas in the reaction.

19 Claims, 7 Drawing Sheets calcination at 1000° C  a) Befor  b)After

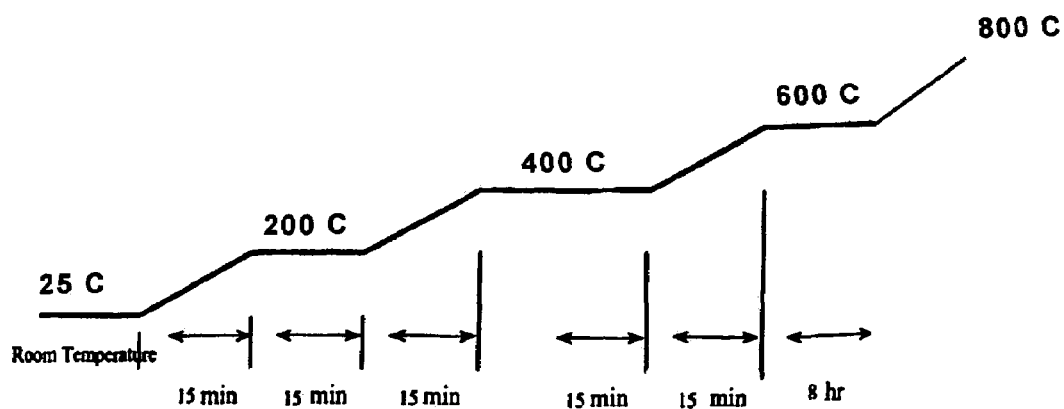
Fig :2
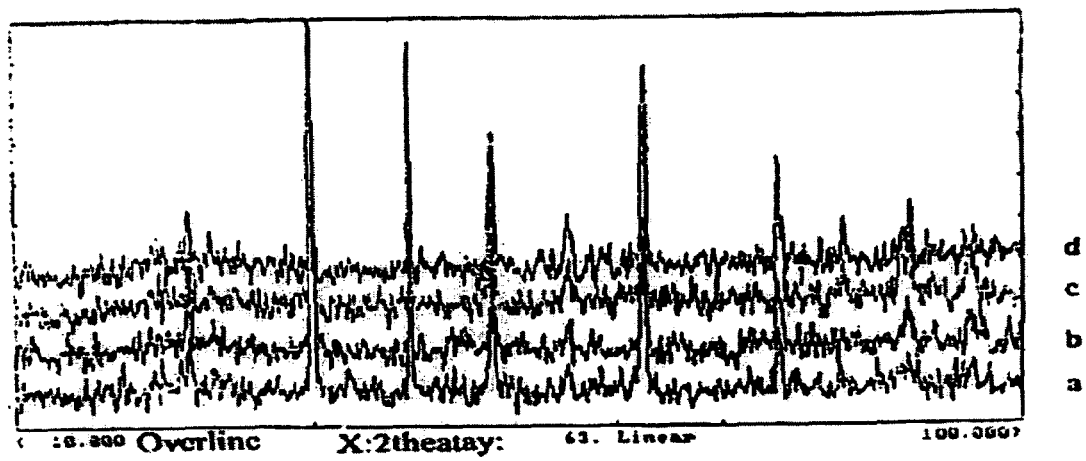
Fig 3: XRD for BaTiO3 after calcination
calcination at 700° C  a) Befor  b)After
calcination at 1000° C  C) Befor  d)After

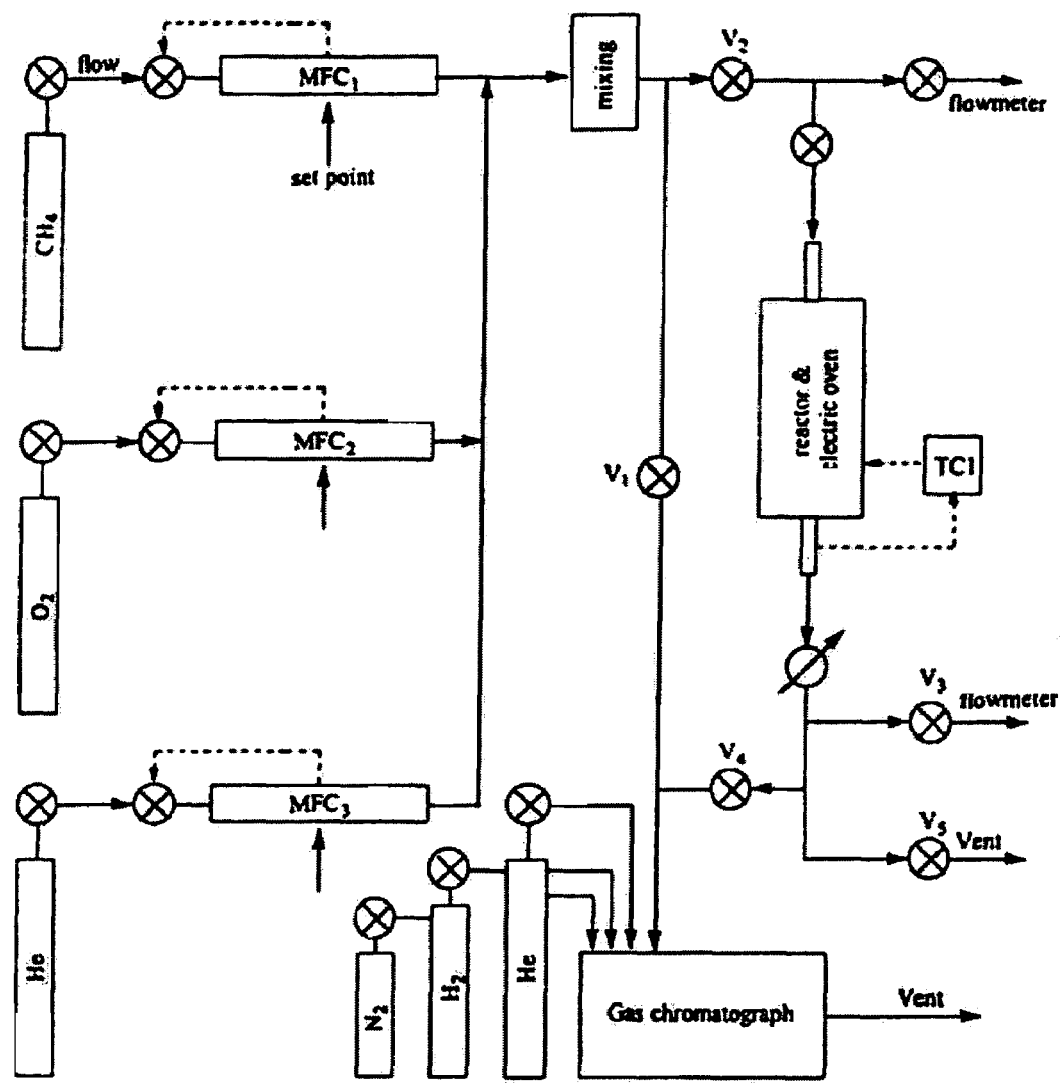
Fig:4

Fig.7 Packed reactor.

PREPARATION OF CATALYST AND USE FOR HIGH YIELD CONVERSION OF METHANE TO ETHYLENE

CROSS-REFERENCES TO RELATED APPLICATIONS

This application is a division of U.S. patent application Ser. No. 10/833,735, filed 28 Apr. 2004, which application claims priority under 35 U.S.C. §119 to Canadian patent application serial no. 2,427,722, filed 29 Apr. 2003, entitled Preparation of Catalyst and Use For High Yield Conversion of Methane to Ethylene, the inventor being Ebrahim Bagherzadeh, an inventor of the present application, and assigned to the assignees of this application, HRD Corp., Houston, Tex. and National Petrochemical Company, Petrochemical Research and Technology Company of Tehran, Iran.

FIELD OF THE INVENTION

The invention relates to the synthesis of higher hydrocarbons from methane. More particularly, the invention relates to methods for forming perovskite catalysts capable of high conversion yield.

BACKGROUND OF THE INVENTION

One of the most outstanding problems in heterogeneous catalysis concerns its use in the partial oxidation of methane to form more reactive chemicals such as ethane, ethylene and other aliphatic hydrocarbons. The oxidative coupling of methane to form ethane and ethylene has been the subject of extensive research following the work of pioneers, Keller and Bhasin, in 1982. Particularly, the conversion of methane to ethylene has been widely investigated. Most researchers have been seeking to increase the efficiency of the conversion.

Much research has been performed and many patents have issued for the use of elements in Groups III, IV, V of periodic table of elements, known as the transition metals. Alkali oxide metals, earth metal oxides and even metal oxide complexes, have been used as catalysts for the conversion of methane to ethylene. Recently, a number of papers regarding methane conversion to ethylene have been published including one by this inventor entitled "Reactivity of $ATiO_3$ perovskites Type of Catalyst (A=Ba, Sr, Ca) on Oxidative Coupling of Methane Reaction", Research Institute of Petroleum Industries (RIPI) NIOC, Vol. 3, No. 10, 1993, in which well defined structures of this catalyst prepared by sol-gel methodologies are discussed. The characterization of these structures has been performed by X-ray diffraction (XRD), scanning electron microscope (S.E.M), the Brunauer, Emmett and Teller method (B.E.T) and confirmation of carbonate present at the surface as determined by Fourier transform Infrared spectroscopy (FTIR).

The kinetics and the mechanism of oxidative coupling of methane using a sodium-manganese oxide catalyst has been studied and confirms the mechanism for other similar structured catalysts. The results of this study was reported in a paper titled "Kinetics and mechanism of oxidative coupling of methane over sodium-manganese oxide catalyst" Rahmatolah et al., Chem Eng Technol 16(1993) 62-67. The reaction using the sodium-manganese oxide catalyst follows the Rideal-Redox mechanism, involving both homogeneous and heterogeneous reaction steps. Gas phase formation of a CH intermediate is a result of a heterogeneous process (surface reaction) and the formation of $C_2+$ hydrocarbons by coupling methyl groups ($CH_3$) is the result of a gas phase homogeneous process.

Catalytic activity for the conversion of methane to ethylene depends upon the surface oxidation rate constant ($K_{ox}$) and the reduction rate constant ($R_{ed}$) between surface oxygen ($O_2$) and methane ($CH_4$). It was shown that the kinetic results of the Mn catalyst could be expressed by the rate equation based on the Rideal-Redox mechanism. Further, as reported in "Oxidative coupling of methane to ethylene over sodium promoted manganese oxide", Golpasha et al., Journal of Engineering, Islamic Republic of Iran, Vol. 3, No.s 3 & 4, November 1990, it was found that the manganese oxide catalyst promoted with sodium and supported on silica exhibits fairly good activity and selectivity towards the synthesis of ethylene from methane at optimum operating conditions having a temperature of 830° C. at atmospheric pressure with a ratio of methane to oxygen of 2/1 ($CH_4/O_2=2$).

Further, the opportunity for commercialization of conversion of natural gas to ethylene through direct conversion reactions was studied in a paper presented by this inventor entitled "An opportunity for commercialization of natural gas to ethylene through direct conversion" at IIES-NIOC 16th World Petroleum Congress, June 2000, Calgary, Alberta, Canada. The paper compared existing processes for gas conversion from various points of view, including: capital requirements, economies of scale, and catalyst performance, and shows there is a possibility for commercialization of oxidation coupling of methane (OCM) over Pyrochlores type catalyst prepared using a sol-gel method. The experimental yield of hydrocarbon product (HC) from the reported catalyst reaction is 18-20% at 750-830° C. at atmospheric pressure over $Sm_2Sn_2O_7$ catalyst (4).

One of these inventors has also reported, in a paper entitled "Direct Oxidative Methane Conversion To Ethylene Using Perovskite Catalyst, 14th World Petroleum Congress, 1994, Stavenger, Norway, the catalytic oxidative coupling of methane over a perovskite catalysts, $CaTiO_3$, prepared using a modified ceramic method resulting in a HC yield of over 18-20% at 830° C. The catalyst was promoted with $Na_4P_2O_7$, which did not considerably improve catalyst performance.

Other technology includes U.S. Pat. No. 4,939,310 which discloses a method for converting methane to a higher HC product using manganese oxide at 500°-1000° C. in contact with the mixture of methane and oxygen. U.S. Pat. No. 4,443,649 discloses a method for conversion of Methane to C, using the same catalyst as U.S. Pat. No. 4,939,310, but further comparisons using Ni, Rh, Pd, Ag, Os, Ir, Pt and Au instead of manganese were carried out. U.S. Pat. Nos. 4,443,649 and 4,544,787 show the use of manganese in different sorts of catalyst. U.S. Pat. No. 5,695,618 teaches the oxidative coupling of methane using an octahedral molecular sieve as the catalyst. U.S. Pat. No. 6,096,934 teaches methane conversion to ethane and ethylene using the same catalyst as U.S. Pat. No. 5,695,618, using steam in the same process. U.S. Pat. No. 5,877,387 utilizes a Pb-substituted hydroxyapatite catalyst for the oxidative coupling of methane which will occur at 600° C. U.S. Pat. No. 4,523,050 for conversion of methane report higher HC. In this patent, a methane and oxygen mixture is contacted with the surface of a solid catalyst containing Si, Mn or manganese silicate. Similarly, in U.S. Pat. No. 4,523,049, methane conversion using a manganese catalyst is promoted using an alkali or alkaline earth metal. U.S. Pat. No. 4,544,784 teaches the conversion of methane into hydrocarbon using catalysts of metal oxides of manganese which incorporate halogen compounds. This strengthened catalyst promotes more efficient conversion and greater contact of the gas mixture with the solid surface of the catalyst. U.S. Pat. No. 5,051,390 teaches the preparation of a cogel catalyst in an aquatic solution. Soluble salts of alkali metals and alkaline earth metals are mixed with soluble metals which are thermally decomposable to form a metal oxide and a hydrolysable silane under such conditions that a homogenous cogel is formed avoiding the formation of precipitates and particles. The catalyst produced is then used for conversion of methane into heavier hydrocarbons like ethylene and ethane.

To date, catalysts prepared using conventional techniques and a variety of constituents are only capable of converting methane to higher hydrocarbons such as ethylene at an efficiency of approximately 20%. Ideally, catalysts for the direct conversion of methane to higher hydrocarbons would be capable of producing said higher hydrocarbons at an efficiency of greater than 20% to provide a commercially viable method for the production of ethylene.

The present inventors have also identified a way to maintain the activity of the catalyst over time, by periodic addition of a halogen source to the OCM reactor over the course of the OCM conversion.

BRIEF SUMMARY OF THE INVENTION

As demonstrated herein, the present invention achieves a catalyst capable of converting methane to ethylene while offering yields of more than 30% of hydrocarbons (HC). In one embodiment, a $BaTiO_3$ catalyst is specifically used in an Oxidative Coupling of Methane (OCM) process wherein one can achieve a yield of ethylene of about 26%. In one embodiment, the method of preparation of the catalyst is based upon a ceramic method (sol-sol) through the mixing of titanium oxide with barium carbonate and tin chloride in an aqueous solvent (deionized water). The resulting slurry is dried and heated and calcined to produce a product perovskite catalyst having the enhanced conversion characteristics.

In a broad aspect of the invention, a method of producing a perovskite catalyst comprises forming a slurry in water of an alkaline earth metal salt, a powdered metal salt and a powdered transition metal oxide, such as by a mixture according to Ba $(1-0.05x)+TiO_2+SnCl_2(0.05X)$ where x is in moles. Evaluations of this formulation were undertaken in the range of Ba $((1-2 \text{ moles}-x)+TiO_2 ((1 \text{ mole}))+SnCl_2(x)$ where x ranges between 0.09 and 0.1 moles, or 0.95 moles Barium per mole of $TiO_2$ to 0.05 moles $SnCl_2$. A polymeric binder is added to the slurry to form a paste. The paste is dried and crushed. In order to convert the metals and metal oxides into a perovskite crystalline structure, the resulting powder is heated using a temperature profile commensurate with the polymeric binder, and then held at a calcination temperature for calcining the comminuted paste to form the perovskite catalyst. The polymeric binder is selected from the group consisting of vinyl acetate dibutyl acrylate and methyl hydroxylethyl cellulose, and a temperature profile that is commensurate with such binders, is to ramp up the temperature in ¼ hour steps as follows: to about 200° C., hold, to about 400° C., hold, to about 600° C., hold, and to ramp to a calcination temperature of about 700°–about 1000° C., preferably about 800° C. The calcined powder is sieved as appropriate, which in an OCM application, is to size the powder to a size that is suitable for use in a catalytic reactor.

The catalyst of the present invention is particularly useful in an OCM process comprising contacting a feed gas stream containing methane and oxygen in an oxidative coupling reactor under oxidative coupling conditions in the presence of the perovskite catalyst.

By periodically adding a halogen source to the OCM reactor over the course of the oxidative coupling reaction, the activity of the catalyst can be maintained over time.

BRIEF DESCRIPTION OF THE SEVERAL VIEWS OF THE DRAWINGS

FIG. 2 is a schematic illustrating the incremental temperature profile during calcination of the catalyst of one embodiment of the present invention;

FIG. 3 is an X-Ray diffractometer printout confirming the crystal structure before calcinations (a),(c) and after (b),(d) calcination at 700° C. and 1000° C., respectively;

FIG. 4 is a schematic of a flow fixed-bed quartz reactor utilized to perform oxidative coupling of methane using the catalysts of the present invention to manufacture ethylene;

DETAILED DESCRIPTION OF THE INVENTION

Figure 1:
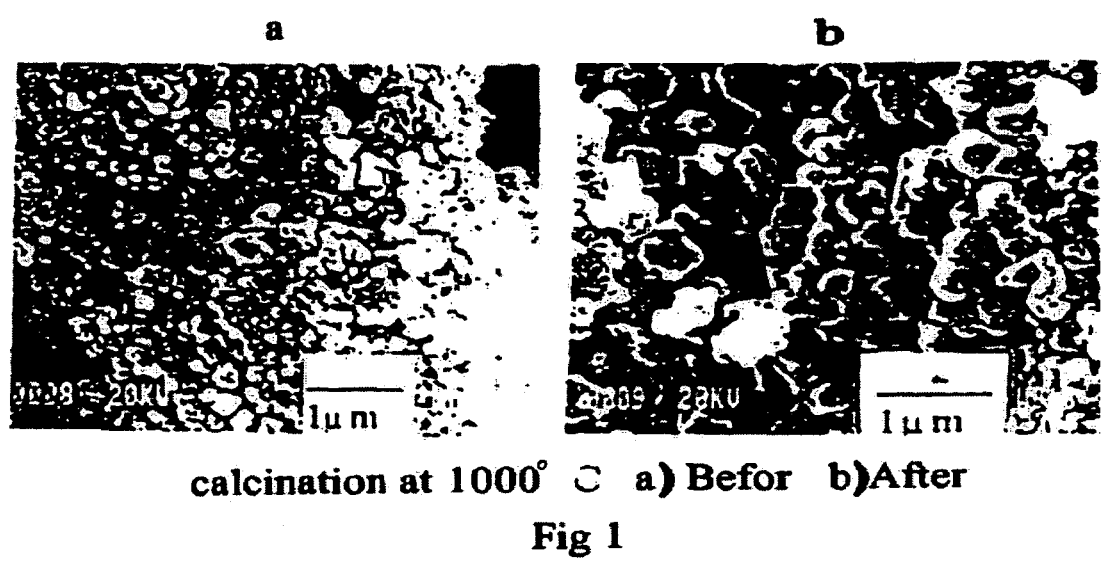
FIGS. 1a and 1b are SEM comparisons of crystal structures before and after applying the temperature profile of FIG. 2.

A perovskite crystal catalyst of the present invention is prepared using a ceramic (sol-sol) method. The present catalyst has improved characteristics over catalysts resulting from the typical sol-sol methodology.

Generally, in one embodiment, the novel catalyst is formed using a sol-sol method initially comprising mixing alkaline earth metal salts with a transition metal oxide in an aqueous solvent (deionized water) to form a slurry. A polymeric binder is added to the slurry to aid in mixing of the constituents and for formation of a paste. The resulting paste is dried and crushed in a mortar. The crushed constituents are sieved to achieve a size compatible with a fixed-bed reactor. The sieved constituents are calcined to remove any undesirable volatiles and combined components. The calcination is performed with staged incremental increases in temperature over time in order to form the perovskite crystalline structure.

The methodology of formation results in a perovskite catalyst of the general formula $ABTiO_3$, the catalyst having a crystal structure which is highly suitable for the partial oxidation of methane to produce ethylene. Preferably A is Sn and B is Ba.

More particularly, a slurry of alkaline earth metal salts and a transition metal oxide is prepared in a solvent of water including distilled or deionized water. The alkaline earth constituents are selected from Ba, Ca, and Sr and combinations thereof. Metal salts are selected from Sn, Mg, Na, Li and Ba.

In one embodiment, barium in the form of carbonate (BaCO$_3$) is mixed in the water with a metal salt such as tin chloride (SnCl$_2$) as a catalyst promoter, and with a transition metal oxide such as titanium oxide (TiO$_3$).

The constituents are mixed vigorously as a slurry. A polymeric binder, such as methyl hydroxylethyl cellulose or vinyl acetate butyl acrylate is added to the slurry. Binder can ensure adequate mixing of the constituents, aid in formation of the paste and improve the final form of catalyst. In a laboratory example, a 50 g sample of constituents were prepared. A cylindrical glass beaker 8.7 cm in diameter and 14.2 cm height was provided with 50 cc of distilled water. An impeller was provided for agitating the water, the impeller comprising a flat blade turbine (3 cm diameter) at rotational speeds of 2000 rpm. The constituents were added to the agitated water for forming the paste. The proportions were prepared according to Ba(1−0.05X)+TiO2+SnCl2 (0.05X), where X=1 mol (i.e. Ba ((0.95 moles))+TiO$_2$((1 mole))+SnCl$_2$(0.05 moles)).

The resulting paste is dried in an oven at approximately 110° C. for a sufficient time to dry the paste. In the example described in the above paragraph, this time period is about 8 hours. The slurry can also be air-dried for a time necessary to evaporate the water. Air-drying can take longer, in the order of 48 hours, dependent upon many ambient conditions and slurry preparation.

Once dried, the paste is crushed. For the above (a bench scale example), the dried paste can be crushed in a mortar, or a press; for forming or obtaining a first pass of powder sized approximately for a catalytic reactor. The crushed powder is then calcined to remove any volatile chemically combined components that are undesirable.

The crushed material contains polymer chains which are thermolabile at calcination temperatures. Accordingly, the crushed material is subjected to incremental increases in temperature over a period of time in a temperature profile empirically determined so as to promote crystal formation, until such time as an appropriate calcination temperature is achieved. The temperature profile is commensurate with the polymeric binder wherein crystal formation is promoted.

Having reference to FIG. 2, the material is typically subjected to staged increases in temperature having both temperature ramping and temperature holding sections. The temperature increases are applied for achieving a temperature profile which is complementary to the polymeric binder used. As known to those skilled in the art, typical burnout rates can increase as the time and temperature increase. For example, in the early rise from ambient temperatures, the rate can be about 200° C. over about ¼ hour with a further ¼ hour hold period. Averaged over the ramp and hold period, the rates range from about 75° C. to about 200° C. over about ½ hour, or about 200° C. (180-220° C.)-about 400° C. per hour. At final calcination temperatures, where the temperatures are higher and decomposition is reduced, higher rates can be applied. Similarly, satisfactory rates include substantially continuous temperature rates of about 400° C. per hour.

As shown in FIG. 2 (not to scale), temperature ramp increases of approximately 200° C. occur over about ¼-½ hour followed by a holding section of a similar ¼-½ hour until a target temperature in the range of about 700°-about 1000° C. is reached, preferably about 800° C. The powdered material is subjected to the final calcination temperature for an additional prolonged duration of about 8 hours or more during which time calcination occurs. Accordingly, in one embodiment of the present invention, starting from a room temperature (ambient temperature) of about 25° C., 7 steps of ¼ hour each will result in a final calcination temperature of about 800° C. in about 1 and ¾ hours.

After calcining, the calcined material is pressed and then crushed under pressure (2-7 tons per cubic centimeter), sieved to select powder having a size compatible for use with a fixed-bed reactor used for the partial oxidation of methane to produce ethylene. Suitable sizing includes material passing a 30 mesh sieve.

Having reference to FIGS. 1a and 1b, scanning electron microscopy and X-ray diffractometry are used to confirm the formation of the desired pseudocubic, orthorhombic perovskite crystals of the resulting catalyst, SnBaTiO$_3$ illustrated before and after calcination.

The perovskite crystal (SnBaTiO$_3$) contains titanium in the form of an octahedron and exhibits reactivity for oxidative coupling of methane as a result of the surface area capable of contact with methane gas and particularly exhibits greater selectivity for ethylene production than do other catalysts of which applicant is aware. While each atom of hydrogen present in the gas is capable of contacting more than one oxygen atom on the crystal surface, contact with only one oxygen atom is likely necessary to form a hydroxyl (OH) necessary to convert methane (CH$_4$) to methyl (CH$_3$) and subsequently to ethylene (C$_2$H$_4$).

The inventors have found that one embodiment of the resulting catalyst, a SnBaTiO$_3$ catalyst, exhibits selectivity for ethylene production of approximately 44%, resulting in a yield of about 29.5% ethylene and heavier compounds and methane conversion of about 67% at a reaction temperature between about 600°-about 800° C. Use of the sol-sol method of production of the SnBaTiO$_3$ catalyst is both reproducible with respect to the catalyst structure, as well as its' ability to produce a reproducible and high ethylene yield compared with conventional catalysts when used for oxidative coupling of methane (OCM).

The OCM reaction is accomplished through dehydrogenation of methane to ethane, in which the bond between one of the hydrogens and the remainder of the methane molecule is weakened. The OCM is conducted in an oxidative coupling reactor under oxidative coupling conditions in the presence of the perovskite catalyst. The weakening of the bond permits partial oxidation of the methane molecule resulting in ethane. The ethane then converts to ethylene. The catalyst is responsible for providing oxygen ions which combine with the hydrogen released during dehydrogenation causing methane (CH$_4$) to convert to a methyl group, CH$_3$. Methyl groups are then free to recombine as ethane, C$_2$H$_6$. The ethane is oxidized to become ethylene C$_2$H$_4$. The free hydrogens combine with oxygen to form water.

In use, the inventors have found that the addition of small quantities of halide, such as chloride, into a feed gas stream in an OCM reaction using the catalyst of the present invention, is found to result in greater stability and to extend the life of the catalyst. It is thought that chlorine, in the gas phase as R—Cl, such as from methane chloride or ethane chloride sources, acts to propagate the radical reaction by modifying the surface properties of the perovskite catalyst. It is also believed that under the reaction conditions the added halogen, such as chloride, forms free radicals or chloride ions that are able to propagate the radical reaction to form, and effect the selectivity to, higher hydrocarbons (C$_2$+).

Other sources of halogen (chloride) included chlorine gas, chloroform, carbon tetrachloride (CCl$_4$), stannous chloride (SnCl$_2$), and hydrochloric acid (HCl). The halogen source was added to the reactor without discontinuing the flow of the inlet gases.

Other potential sources of chloride that could be used include methylene chloride, ethylene dichloride and most other sources of chloride, provided that the source does not introduce other components, such as concentrations of other cations, such as, for example only and not intended as a limitation, sodium, Li, Sn, Ca, Ba, Pb, Ir, La, Rb, Rh, actinides, other lanthanides, various olefins, or other components whose presence could be detrimental to the OCM process, either as poisons to the catalyst, interfere with the inlet gases, or affect the end products of the process.

Ethylene is recognized as an industrially important compound, for it is a precursor for the synthesis of numerous other compounds, ranging from monomers such as styrene, to polymers, copolymers and interpolymers of ethylene with other olefins. Among the resulting products from reaction of ethylene with other substrates include such diverse products as polyethylenes, ethylene glycols, ethylene dibromide, ethylene dichloride, ethylbenzene, ethylene oxide, plastics such as polystyrene, and the like.

The potential substrates with which the ethylene and other hydrocarbons produced in the OCM reactor could be reacted with to form such products include one or more compounds such as aliphatics such as ethylene, propylene, butylene and the like; alkanes such as ethane, propane, butane, pentane and the like; alkynes; aromatic compounds such as benzene or toluene and their derivatives; additional oxygen or chlorine gases, other halogens such as bromine, fluorine and iodine.

While many processes require the use of ethylene in concentrations of greater than 90% purity, some of these downstream processes should be capable of utilizing ethylene at the concentrations obtained as a result of the OCM reactions described herein.

EXAMPLE 1

Oxidative Coupling of Methane

A variety of catalysts were prepared using the sol-sol methodology of the present invention. Different alkali earth metals were applied for use in a direct conversion reaction for the production of ethylene from methane. The catalysts were prepared employing the basic perovskite crystal formula, $ABTiO_3$, so as to determine the optimum perovskite catalyst which is capable of reproducibly producing the greatest yield of ethylene. Combinations were tried including A=tin (Sn) and wherein B was selected from=Ca,Sr,Ba or combinations thereof.

Evaluations of this formulation were undertaken in the range of Ba ((1-2 moles–x)+$TiO_2$ ((1 mole))+$SnCl_2$(x) where x ranges between 0.09 and 0.1 moles, or 0.95 moles Barium per mole of $TiO_2$ to 0.05 moles $SnCl_2$.

With reference to FIG. 4, the reactor experiments were carried out in a flow fixed-bed quartz reactor having a diameter of 10 mm at a temperature ranging from between about 500° C.-about 1000° C., but preferably between about 700° C.-about 800° C. The reactor was operated at atmospheric pressure. A total feed gas flow of methane/oxygen in a 2:1 ratio was provided at a range of 10-12 liters/hour/gram of catalyst and a gas hourly space velocity (GHSV) in a range of 200-20,000 per hour. The process was operated continuously with the products being analyzed using a gas chromatograph (GC-HP6890 with HP-PLOT-Q) and a 5 Å molecular sieve column online.

Table 1 illustrates the variety of catalysts prepared and tested and the percentage methane converted, the percentage ethylene yield and the percentage HC yield per mole, for each test.

TABLE 1

| Example Test | Catalyst X = 1 mol | $CH_4$ Conv. | $C_2H_4$ Yield | HC Yield |
|---|---|---|---|---|
| 1 | $BaTiO_3$ | 20.48 | 9.43 | 13.73 |
| 2 | $Ba_{(1-0.05x)}Ca_xTiO_3$ | 34.13 | 14.34 | 19.02 |
| 3 | $Ba_{(1-0.05x)}Sr_xTiO_3$ | 34.15 | 15.29 | 18.42 |
| 4 | $Ba_{(1-0.1x)}Ca_{0.05x}TiO_3 + 0.05xMgCl_2$ | 55.43 | 12.79 | 17.09 |
| 5 | $Ba_{(1-0.1x)}Ca_{0.05x}TiO_3 + 0.05xLiCl$ | 29.16 | 11.28 | 16.01 |
| 6 | $Ba_{(1-0.05x)}TiO_3 + 0.05xNaCl$ | 27.29 | 11.22 | 21.51 |
| 7 | $Ba_{(1-0.5x)}TiO_3 + 0.05xSnCl_2$ | 66.63 | 29.26 | 34.7 |
| 8 | $Ca_{(1-0.5x)}TiO_3 + 0.05xNaCl$ | 37.74 | 14.97 | 15.77 |
| 9 | $Ba_{(1-0.1x)}Ca_{0.05x}TiO_3 + 0.05xBaCl_2$ | 29.69 | 11.99 | 16.65 |

Table 1: Experimental Parameters: Feed $CH_4/O_2$ = 2:1, 100 ml/min, GHSV = 12000 $h_{-1}$, catalyst 1 g = 3 $cm_3$ 30 mesh, 24 mm outer diameter quartz reactor, $O_2$ conversion 99%, temperature 775° C., pressure <1 bar.

It was found that the alkali earth methods were of different activities, particularly as follows: Ca<Sr<Ba. The amount of methane converted and the yields were highest when chlorine was provided and the catalyst that provided the optimum results was one in which barium was the alkaline earth metal and tin (Sn) was used as the promoter. In particular, the catalyst used in Sample #7 (Table 1) was formed by combining 187.5 grams of $BaCO_3$ with 11.1 grams of $SnCl_2.2H_2O$ and 80.0 grams of $TiO_2$ and processed, calcined and pressed (at 7 tons per square inch) in a manner as previously described.

Methane provided in the feed gas and used in the reaction can be totally pure, or may be mixed with other hydrocarbon gases like ethane up to $C_2+$ having a ratio of methane to oxygen of 2:1 on a molar basis having a total flow in the range of 10-12 liters.$h^{-1}$.$grcat^{-1}$. Additionally, He or $N_2$ gases, which act as diluters, can be used and the reaction is carried out at atmospheric pressure. The products of the direct conversion of methane are: ethane, ethylene, carbon monoxide, carbon dioxide and water.

The degradation of the catalyst is controlled by the presence of halogenated components in the feed stream.

The resulting catalyst has a pseudocubic and perovskite crystal shape which is stable before and after calcinations.

EXAMPLE 2

Pilot Scale Oxidative Coupling of Methane: Effect of Halogen Addition

In this example, and in Example 3, OCM was performed using a pilot reactor with approximately 30.5 grams of a catalyst prepared from a mixture of Barium carbonate, Tin chloride and Titanium oxide, combined in a ratio of 39.3 grams; 11.4 grams; 19.2 grams. The resulting catalyst was then pelletized under 5.5 tons/$cm^3$ and crushed into particles of between 1.96-3.96 mm diameter.

Figure 7:
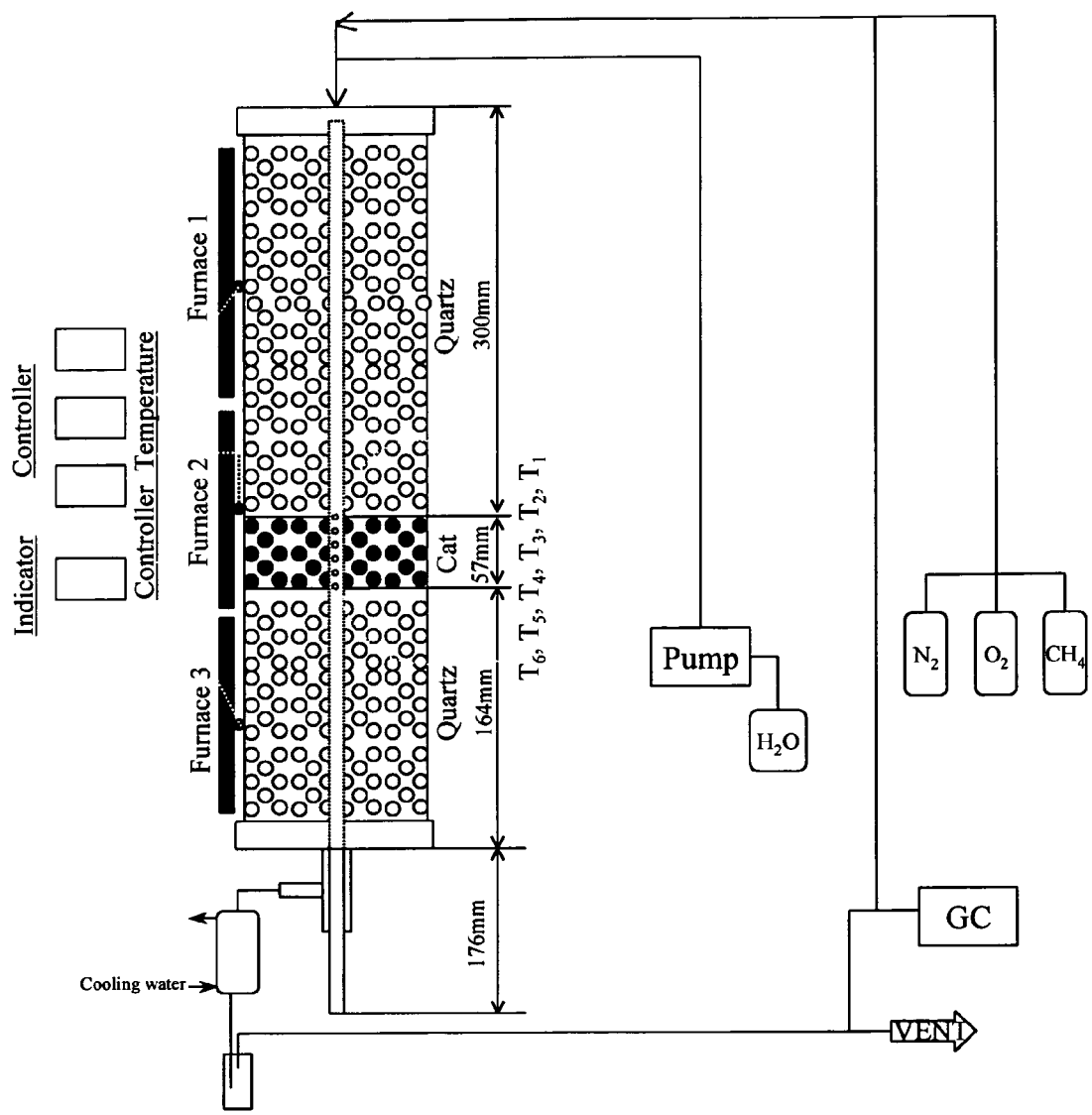
FIG. 7 is a schematic of the pilot reactor utilized to perform oxidative coupling of methane using a catalyst of one embodiment of the present invention.

A model SS316 reactor tube having dimensions of 25 mm (O.D., 21 mm I.D.) by 490 mm in length was fitted with a quartz liner, and quartz packing, and the catalyst packed towards the middle of the reactor tube without dilution, as shown in FIG. 7 (illustrating top gas feed). The effects of both bottom and top gas feed injection were evaluated; the best results (Table 2) were achieved using bottom gas feed. The top and bottom portions of the reactor were packed with quartz particles of diameter ranging from 1.98-3.96 mm.

Figure 5:
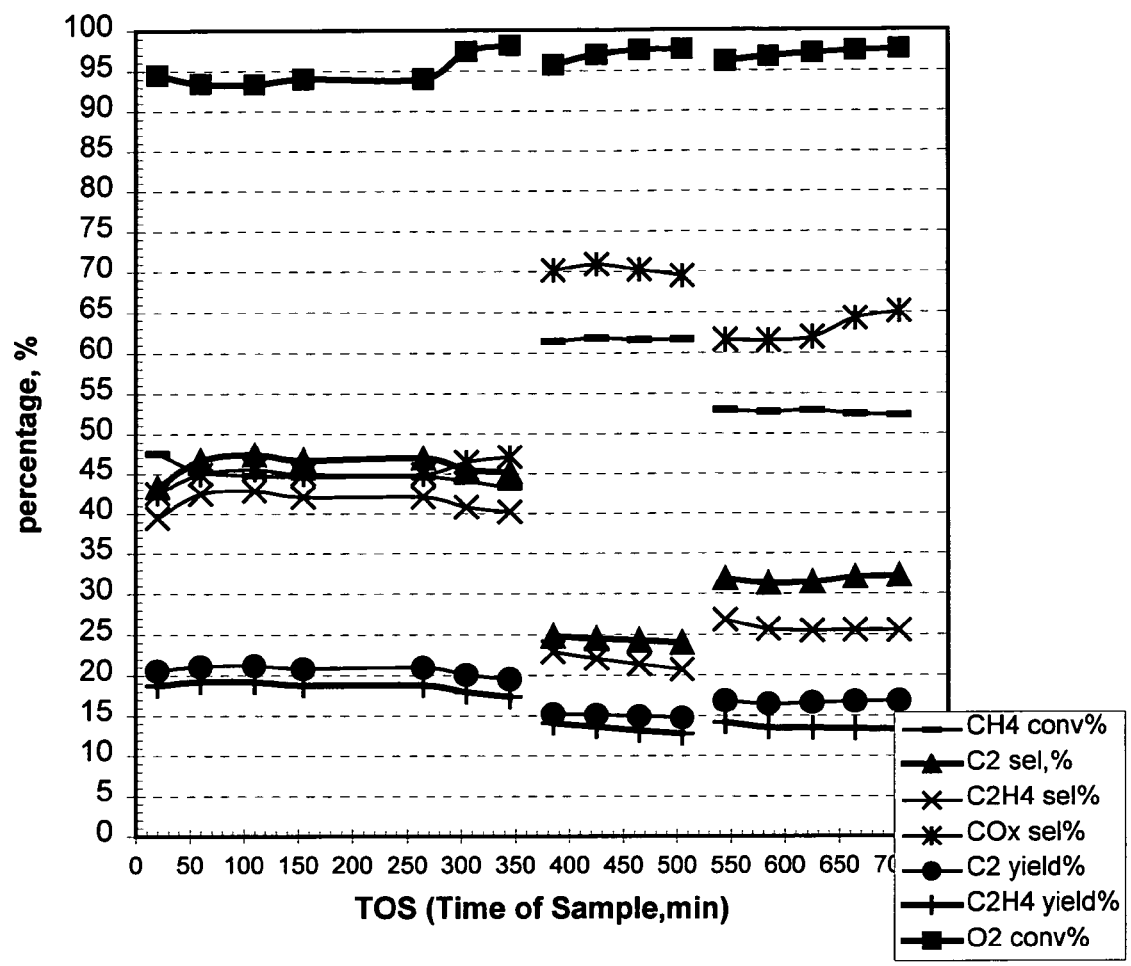
FIG. 5 shows the effects of carbon tetrachloride ($CCl_4$) addition on the oxidative coupling of methane to ethylene as a function of time.

In this example, a halogen, in the form of carbon tetrachloride ($CCl_4$) was injected into the reactor inlet at various times, samples taken at various times of sample (TOS), and the percent conversion (conv.), selectivity (sel.) or yield of particular products was determined, and shown in FIG. 5.

For this example, the parameters were as follows:
Catalyst particle size: 2-4 mm (1.96-3.96 mm);
Quantity of catalyst used: 20 cc/30.5 grams.
Methane/Oxygen/Nitrogen: molar ratio of inlet gas: $CH_4$:$O_2$:$N_2$=2:1:4, or 1:1:2. or 2:1.5:4, WHSVCl=0.16; GHSV=1175 or 1331, or 1265; 18 mm QTL reactor, with $CCl_4$ (0.2 microliters (μl)) being injected every 2 hours to the inlet of the reactor.
GHSV was adjusted from 1175 to 1331 or 1265 at selected times, and the breaks shown in the graphical data indicate where changes in the GHSV flow rate occurred.

Figure 6:
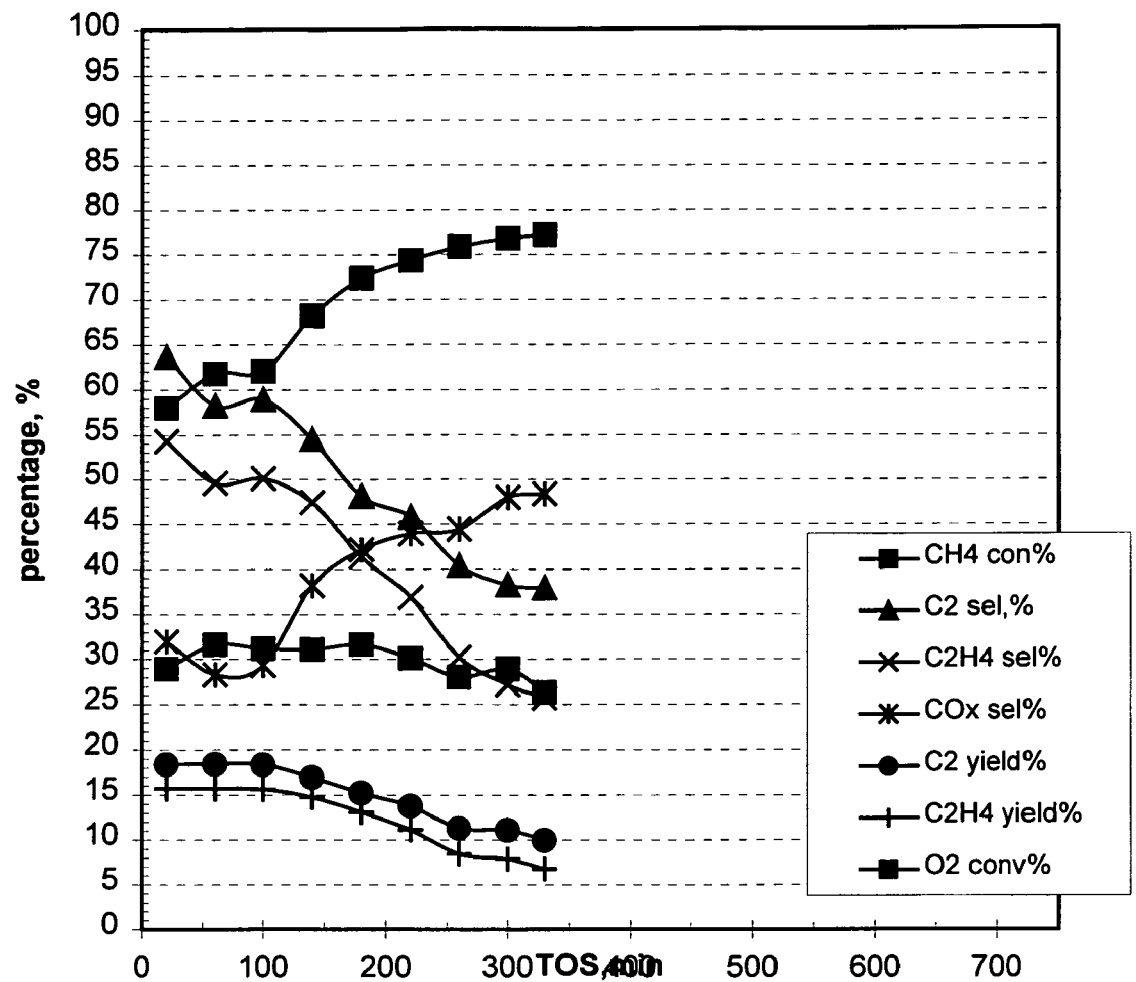
FIG. 6 shows the oxidative coupling of methane to ethylene in the absence of carbon tetrachloride ($CCl_4$), as a function of time.

The data indicates that the presence of a halogen in the reactor maintains the conversion of methane to ethylene over a longer time period (FIG. 5) compared to the absence of the halogen (FIG. 6). The ethylene selectivity ranged between 40-45% during the early phases of the experiment, to between about 20-30% during its later stages (FIG. 5). Ethylene yield was about 20% during the early phases.

EXAMPLE 3

For this example, the same catalyst as used in Example 2 was employed, but not diluted; no halogen was added to the reactor.

For this example, the parameters were as follows:
Methane/Oxygen/Nitrogen molar ratio of inlet gas: $CH_4$:$O_2$:$N_2$ was 2:1:8.
GHSV=5123;
WHSVCl=0.44;
Quartz-lined reactor, no $CCl_4$ added.

EXAMPLE 4

Effect of Carbon Dioxide

Carbon dioxide ($CO_2$) gas was added to the mixture of inflow gases, such that the inflow gas mixture comprised $CH_4$:$O_2$:$N_2$:$CO_2$ in a ratio of 2:1:1:2, at a GHSV of 3300 and then 1550; WHSV cl 0.45/0.21, and a carbon tetrachloride ($CCl_4$) bubble injected with nitrogen for 3 minutes at every hour. The catalyst, sample #7 (from Table 1) was 13 cc/22.6 g undiluted.

Figure 8:
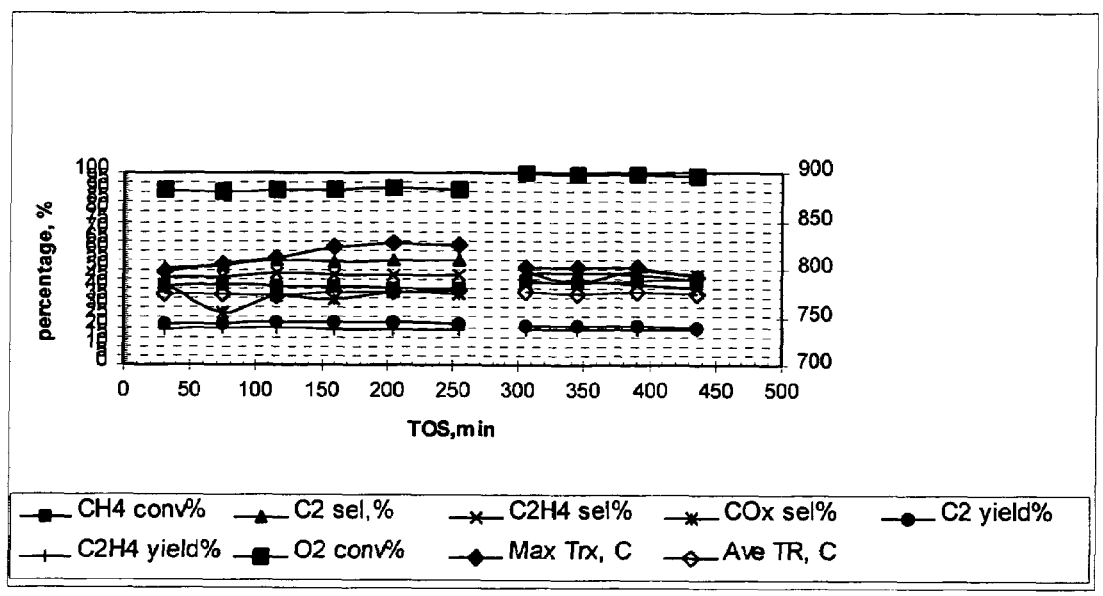
FIG. 8 shows the effects of carbon dioxide ($CO_2$) addition to the feed gas on the oxidative coupling of methane to ethylene as a function of time.

The results (FIG. 8) indicate that a greater than 90% conversion of methane occurred, with an ethylene yield of greater than 30% could be effected, and sustained over the course of the OCM reaction.

EXAMPLE 5

Effect of Water Addition

In this example, the reactor was heated at its top, middle and bottom sections with three independent furnaces (Furnace 1, Furnace 2 and Furnace 3), as shown in FIG. 7. The reactor was first heated up to 450° C. with nitrogen flowing at about 100 ml/min. At a temperature of 450° C. and above, the reactor was heated up with the reactant mixture, which included water as specified below: Water was pumped in using Pump shown in FIG. 7. The feed gases were nitrogen, ($N_2$) oxygen ($O_2$) and methane ($CH_4$) (FIG. 7).

Nitrogen: 150 ml/min (gas flow rates are given at 0° C. and 1 atm.)
Oxygen: 201 mm/min
Methane: 407 ml/min
Water: 76.5 g/hr=1587 ml/min (vapor, calculated at 0° C. and 1 atm)

The reactant mixture (in moles) is $N_2$:$O_2$:$CH_4$:$H_2O$=1.5:2:4:15.9 (6.40, 8.57, 17.36, and 67.67 mol %, respectively).

The reactor was controlled to a temperature of between 700° and 800° C. Samples were analyzed using the Gas Chromatograph (GC), as described previously.

The results (Table 2) suggest that chloride was being stripped from the catalyst during the reaction process.

TABLE 2

| TOS, min | $CH_4$ con % | $O_2$ conv % | $C_2$ sel, % | $C_2H_4$ sel % | COx sel % | $C_2$ yield % | $C_2H_4$ yield % |
|---|---|---|---|---|---|---|---|
| A | 20 | 28.11 | 44.75 | 76.91 | 59.55 | 18.77 | 21.62 | 16.74 |
| B | 60 | 38.39 | 69.93 | 61.56 | 51.35 | 27.48 | 23.64 | 19.71 |

There are alternative methods of adding halogen to the reactor, such as a continuous or "slug" (periodic additions of a quantity of agent) injection. During the reaction of this example, Carbon tetrachloride ($CCl_4$) was injected with a micro-syringe at 0.2 microliters (μl) every two hours in order to keep the catalyst activity high.

What is claimed is:

1. A method of oxidative coupling of methane for the formation of heavier hydrocarbons, the method comprising the steps of:
   producing a perovskite catalyst, the catalyst produced by a process comprising:
      forming an aqueous slurry comprising an alkaline earth metal salt, a powdered metal salt and a powdered transition metal oxide,
      wherein the alkaline earth metal is selected from the group consisting of barium, calcium and strontium salts, and wherein the metal oxide is titanium oxide;
      adding a polymeric binder to the slurry to form a paste;
      drying the paste for forming a powder;
      heating the powder at increasing temperatures at a predetermined profile commensurate with the polymeric binder; and
      calcining the heated powder; and
   contacting a feed gas stream containing methane and oxygen in an oxidative coupling reactor under oxidative coupling conditions in the presence of the perovskite catalyst.

2. The method of claim 1, further comprising adding either a halogen or carbon dioxide into the feed gas stream, and wherein the halogen is added at timed intervals during the oxidative coupling.

3. The method of claim 2, wherein the halogen is chloride.

4. The method of claim 3, wherein the chloride in the gas stream is selected from the group consisting of methane chloride, ethane chloride, chlorine gas, chloroform, stannous chloride ($SnCl_2$), hydrochloric acid (HCl), or carbon tetrachloride ($CCl_4$).

5. The method of claim 4, wherein the chloride in the gas stream is carbon tetrachloride ($CCl_4$).

6. The method of claim 3, further comprising the step of reacting the higher hydrocarbons with one or more compounds selected from the group consisting of the higher hydrocarbons, ethylene, propylene, butylene, benzene, styrene, chlorine, oxygen, and olefins.

7. The method of claim 6, wherein the slurry comprises a mixture including Ba (0.5x-1x)+TiO$_2$, wherein x is in moles.

8. The method of claim 6, wherein the slurry comprises a mixture including Ba (0.5x-1x)+TiO$_2$ and either Ca$_x$ or Sr$_x$, wherein x is in moles.

9. The method of claim 7, wherein the slurry is formed by a mixture according to Ba (0.5-0.95x)+TiO$_2$+R(0.05-0.5x), wherein x is in moles, and wherein R is selected from the group consisting of BaCl$_2$, LiCl, MgCl$_2$, NaCl, and SnCl$_2$.

10. The method of claim 7, wherein the slurry comprises a mixture including Ba (0.5-0.95x)+TiO$_2$+SnCl$_2$(0.05x), wherein x is in moles.

11. The method of claim 8, herein the slurry is formed by a mixture according to Ba (0.95x)+TiO$_2$+SnCl$_2$(0.05x), wherein x is in moles.

12. The method of claim 6, herein the polymeric binder is selected from the group of polymer binders consisting of vinyl acetate dibutyl acrylate and methyl hydroxyl ethyl cellulose.

13. The method of claim 12, further comprising sizing the catalyst to a size suitable for the oxidative coupling reactor.

14. A method of oxidative coupling of methane for the formation of heavier hydrocarbons, the method comprising the steps of:
   producing a perovskite catalyst, the catalyst produced by a process comprising:
      forming an aqueous slurry comprising an alkaline earth metal salt, a powdered metal salt and a powdered transition metal oxide, wherein the alkaline earth metal is selected from the group consisting of calcium (Ca), barium (Ba) and strontium (Sr) salts, wherein the metal salt is tin (Sn); wherein the transition metal oxide is titanium oxide;
      drying the slurry to form a powder;
      heating the powder at increasing temperatures at a predetermined profile; and
      calcining the heated powder to produce the perovskite catalyst,
      wherein the perovskite catalyst comprises a mixture including Ba+TiO$_2$+R, wherein R is tin (Sn); and
   contacting a feed gas stream containing methane and oxygen in an oxidative coupling reactor under oxidative coupling conditions in the presence of the perovskite catalyst.

15. The method of claim 14, further comprising adding either a halogen or carbon dioxide into the feed gas stream, and wherein the halogen is added at timed intervals during the oxidative coupling.

16. The method of claim 15, wherein the halogen is chloride.

17. The method of claim 16, wherein the chloride in the gas stream is selected from the group consisting of methane chloride, ethane chloride, chlorine gas, chloroform, stannous chloride (SnCl$_2$), hydrochloric acid (HCl), or carbon tetrachloride (CCl$_4$).

18. The method of claim 17, wherein the chloride in the gas stream is carbon tetrachloride (CCl$_4$).

19. The method of claim 15, further comprising the step of reacting the higher hydrocarbons with one or more compounds selected from the group consisting of the higher hydrocarbons, ethylene, propylene, butylene, benzene, styrene, chlorine, oxygen, and olefins.

* * * * *